(12) United States Patent
Willbold et al.

(10) Patent No.: US 9,051,364 B2
(45) Date of Patent: Jun. 9, 2015

(54) COMPOSITION FOR PRODUCING ANTI-AMYLOID BETA PEPTIDE ANTIBODIES WITH D-PEPTIDES

(75) Inventors: Dieter Willbold, Juelich (DE); Carsten Korth, Duesseldorf (DE); Andreas Mueller-Schiffmann, Odenthal (DE); Susanne Aileen Funke, Titz (DE)

(73) Assignees: FORSCHUNGSZENTRUM JUELICH GMBH, Juelich (DE); HEINRICH-HEINE-UNIVERSITAET, Duesseldorf (DE)

( * ) Notice: Subject to any disclaimer, the term of this patent is extended or adjusted under 35 U.S.C. 154(b) by 346 days.

(21) Appl. No.: 13/129,579

(22) PCT Filed: Nov. 17, 2009

(86) PCT No.: PCT/EP2009/065308
§ 371 (c)(1),
(2), (4) Date: May 17, 2011

(87) PCT Pub. No.: WO2010/057882
PCT Pub. Date: May 27, 2010

(65) Prior Publication Data
US 2011/0243949 A1 Oct. 6, 2011

(30) Foreign Application Priority Data
Nov. 19, 2008 (DE) .......................... 10 2008 037 564

(51) Int. Cl.
| | |
|---|---|
| *A61K 39/00* | (2006.01) |
| *C07K 16/44* | (2006.01) |
| *C07K 7/08* | (2006.01) |
| *C07K 16/18* | (2006.01) |
| *C07K 14/47* | (2006.01) |

(52) U.S. Cl.
CPC ............. *C07K 16/18* (2013.01); *A61K 39/0007* (2013.01); *A61K 2039/505* (2013.01); *A61K 2039/6081* (2013.01); *C07K 7/08* (2013.01); *C07K 14/4711* (2013.01)

(58) Field of Classification Search
CPC ........... A61K 39/0007; A61K 38/1709; A61K 38/10; A61K 38/04; C07K 7/08; C07K 14/47; C07K 14/4711; C07L 16/18; C07L 7/00
See application file for complete search history.

(56) References Cited

U.S. PATENT DOCUMENTS

| | | | |
|---|---|---|---|
| 6,261,569 B1 | 7/2001 | Comis et al. | |
| 6,689,752 B2 | 2/2004 | Findeis et al. | |
| 6,849,714 B1 * | 2/2005 | Bridon et al. | 530/335 |
| 2003/0068325 A1 | 4/2003 | Wang | |
| 2008/0171341 A1 | 7/2008 | Orser et al. | |

FOREIGN PATENT DOCUMENTS

| | | |
|---|---|---|
| WO | WO 94/05311 A1 | 3/1994 |
| WO | WO 00/52048 A1 | 9/2000 |
| WO | WO 02/081505 A2 | 10/2002 |
| WO | WO 02/096350 A2 | 12/2002 |
| WO | WO 2005058941 A2 * | 6/2005 |

OTHER PUBLICATIONS

Bianchi E et al. (2009) A peptide vaccine based on retro-inverso beta-amyloid sequences fails to elicit a cross-reactive immune response. Adv. Exp. Med. Biol. 611:363-364.*
English language machine translation for WO 02/081505 A2, provided by EPO Espacenet, retrieved Jul. 13, 2012.*
Muller S. (1998) The potential of retro-inverso peptides as synthetic vaccines. Exp. Opin. Invest. Drugs, 7(9):1429-1438.*
Nelson AR et al. Long-term treatments with an amyloid beta 42-binding D-amino acid peptide reduce amyloid deposition and inflammation in AD model mice. Society for Neuroscience Annual Meeting 2008, Poster Abstract # 542.14/O10, Nov. 18, 2008.*
Van Groen T et al. Treatment with an amyloid beta-42-binding D-amino acid peptide decreases amyloid deposition and reduces plaques in APP/PS1 mutant mice. Society for Neuroscience Annual Meeting 2008, Poster Abstract # 542.15/O11, Nov. 18, 2008.*
Vickers JC (2002) Drugs Aging. 19(7):487-494.*
Apotolopoulous V & Lasoura E. (2004) Noncanonical peptides in complex with MHC class I. Expert Rev. Vaccines, 3(2):151-162.*
Zurbriggen R et al. (2005) Virosome-based active immunization targets soluble amyloid species rather than plaques in a transgenic mouse model of Alzheimer's disease. J. Mol. Neurosci. 27:157-166.*
C. Nicolau et al.: "A Liposome-based Therapeutic Vaccine Against Beta-Amyloid Plaques on the Pancreas of Transgenic Norba Mice", Proceedings of the National Academy of Sciences of the United States (PNAS), National Academy of Science, US LNKD-DOI: 10.1073/PNAS.022627199, vol. 99, No. 4, pp. 2332-2337, XP009062068, ISSN: 0027-8424 (Feb. 19, 2002).
B. Solomon et al.: "Disaggregation of Alzheimer Beta-Amyloid by Site-Directed mAb", Proceedings of the National Academy of Sciences of the United States (PNAS), National Academy of Science, US-LNKD-DOI: 10.1073/PNAS.94.8.4109, vol. 94, pp. 4109-4112, XP002942849, ISSN: 0027-8424 (Apr. 1997).
K. Wiesehan: "Indentification and characterization of a specific ligand for the Alzheimer amyloid-.beta.-peptide (A.beta.)", Berichte des Forschungszentrum Juelich, JUEL-4024, I-VII, 1-143 CODEN: FJBEE5; ISSN: 0944-2952, XP002569790, pp. 70, 119 (2003).
M. A. Findeis: "Modified peptide inhibitors of amyloid-beta-peptide polymerization", Biochemistry, American Chemical Society, Easton, PA., US, vol. 38, No. 21, pp. 6791-6800, XP002143947, ISSN: 0006-2960 (May 5, 1999).
L. O. Tjernberg et al.: "Controlling Amyloid Beta-Peptide Fibril Formation with Protease-Stable Ligands", Journal of Biological Chemistry, American Society of Biolochemical Biologists, Birmingham, US, vol. 272, No. 19, pp. 12601-12605, XP002050230, ISSN: 0021-9258 (May 9, 1997).

(Continued)

*Primary Examiner* — Kimberly A Ballard
(74) *Attorney, Agent, or Firm* — Abel Law Group, LLP

(57) ABSTRACT

A composition includes D-peptides or antibodies to at least one of to prevent a disease and to treat the disease, wherein the D-peptides interact with an amyloid peptide and the antibodies bind to both the D-peptide and the amyloid peptide.

8 Claims, 2 Drawing Sheets

(56) References Cited

OTHER PUBLICATIONS

C. A. Lemere et al.: "Novel Aβ immunogens: Is shorter better?", Current Alzheimer Research, vol. 4, No. 4, pp. 427-436, XP008122216, ISSN: 1567-2050 (Sep. 4, 2007).

C. Cao et al.: "Mutant Amyloid-beta-sensitized dendritic cells as Alzheimer's disease vaccine", Journal of Neuroimmunology, Elsevier Science Publishers BV, XX LNKD-DOI: 10.1016/J.JNEUROIM.2008.05.017, vol. 200, No. 1-2, pp. 1-10, XP024100005, ISSN: 0165-5728 (Aug. 30, 2008).

F. Bard et al.: "Epitope and isotype specificities of antibodies to β-amyloid peptide for protection against Alzheimer's disease-like neuropathology", PNAS, vol. 100, No. 4, pp. 2023-2028 (Feb. 18, 2003).

C. P. Ferri et al.: "Global prevalence of dementia: a Delphi consensus study", Lancet. 366 (9503): 2112-2117, pp. 1-12 (Dec. 17, 2005).

D. M. Walsh et al.: "Aβ Oligomers—a decade of discovery", Journal of Neurochemistry, vol. 101, pp. 1172-1184 (2007).

D. Schenk et al.: "Immunization with amyloid-β attenuates Alzheimer-desease-like pathology in the PDAPP mouse", Nature, vol. 400, pp. 173-177 (Jul. 8, 1999).

D. L. Brody et al.: "Active and Passive Immunotherapy for Neurodegenerative Disorders", Annual Reveiws in Neuroscience, 31: 175-193, pp. 1-20 (2008).

R. Dodel et al.: "Human Antibodies against Amyloid β Peptide: A Potential Treatment for Alzheimer's Disease", Annals of Neurology, vol. 52, No. 2, pp. 253-256 (Aug. 2002).

A.S. Gardberg et al.: "Molecular basis for passive immunotherapy of Alzheimer's disease", PNAS, vol. 104, No. 40, pp. 15659-15664 (Oct. 2, 2007).

E. Head et al.: "A Two-Year Study with Fibrillar β-Amyloid (Aβ) Immunization in Aged Canines: Effects on Cognitive Function and Brain Aβ", The Journal of Neuroscience, vol. 28(14), pp. 3555-3566 (Apr. 2, 2008).

D. H. Cribbs et al.: "All-D-Enantiomers of β-Amyloid Exhibit Similar Biological Properties to All-L-β-Amyloids", The Journal of Biological Chemistry, vol. 272, No. 11, pp. 7431-7436 (1997).

W. P. Esler et al.: "Stereochemical Specificity of Alzheimer's Disease β-Peptide Assembly", Biopolymers, vol. 49, pp. 505-514 (1999).

M. Lee et al.: "Aβ42 Immunization in Alzheimer's Disease Generates Aβ N-Terminal Antibodies", Americal Neurological Association, vol. 58, No. 3, pp. 430-435 (Sep. 2005).

M. HV Van Regenmortel et al.: "D-peptides as immunogens and diagnostic reagents", Current Opinion in Biotechnology, vol. 9, pp. 377-382 (1998).

C. Korth et al.: "Monoclonal Antibodies Specific for the Native, Disease-Associated Isoform of the Prion Protein", Methods in Enzymology 309, pp. 106-122 (1999).

V. Geylis et al.: "Human monoclonal antibodies against amyloid-beta from healthy adults", Neurobiology of Aging, vol. 26, pp. 597-606 (2005).

\* cited by examiner

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial
<220> FEATURE:
<223> OTHER INFORMATION: D3-Peptid (Willbold); D-amino acid

<400> SEQUENCE: 1

Arg Pro Arg Thr Arg Leu His Thr His Arg Asn Arg
1               5                   10

<210> SEQ ID NO 2
<211> LENGTH: 16
<212> TYPE: PRT
<213> ORGANISM: Artificial
<220> FEATURE:
<223> OTHER INFORMATION: retro-inverso-Abeta (1-16); riAbeta (1-16);
      D-amino acid

<400> SEQUENCE: 2

Lys Gln His His Val Glu Tyr Gly Ser Asp His Arg Phe Glu Ala Asp
1               5                   10                  15
```

COMPOSITION FOR PRODUCING ANTI-AMYLOID BETA PEPTIDE ANTIBODIES WITH D-PEPTIDES

CROSS REFERENCE TO PRIOR APPLICATIONS

This application is a U.S. National Phase application under 35 U.S.C. §371 of International Application No. PCT/EP2009/065308, filed on Nov. 17, 2009 and which claims benefit to German Patent Application No. 10 2008 037 564.0, filed on Nov. 19, 2008. The International Application was published in German on May 27, 2010 as WO 2010/057882 A2 under PCT Article 21(2).

FIELD

The present invention provides a composition comprising D-peptides or antibodies for use as a therapeutic in the treatment of diseases involving aberrant protein aggregation or multimerization. The present invention further provides a process for preparing the composition and also to the use thereof.

SEQUENCE LISTING

The Sequence Listing associated with this application is filed in electronic form via EFS-Web and is hereby incorporated by reference into this specification in its entirety. The name of the text file containing the Sequence Listing is Sequence_Listing_01_07_2011_ST25. The size of the text file is 925 Bytes, and the text file was created on Jul. 1, 2011.

BACKGROUND

Protein aggregation diseases or amyloid degeneration is a heterogeneous group of clinical states which have in common the criterion of, in many cases but not exclusively, a protein specific to each case being deposited extracellularly (systemically or locally) in the ordered conformation of a beta sheet structure. The group of protein aggregation diseases or protein misfolding diseases also includes Alzheimer's disease. Alzheimer's disease (in Latin: Morbus Alzheimer) in its most common form occurs in persons over the age of 65 as a neurodegenerative disorder. The pathogenesis thereof is characterized by an impairment of cognitive ability, which is usually accompanied by a decline in daily activities, with behavioral disorders and neuropsychological symptoms. The patients at an advanced stage forget long-known skills and no longer recognize people to whom they are close. Life expectancy after diagnosis of Alzheimer's disease is, from a statistical perspective, on average about seven to ten years.

Ferri et al. (Lancet. 366, No. 9503, 2005, pp. 2112-7) describe that in 2005, about 24 million people suffered from dementia, of which about 60% could be attributed to Alzheimer's disease). Alzheimer's disease is currently the most common form of dementia for which no causal therapy at present exists.

A pathological sign of Alzheimer's disease, which can be determined even before the first clinical symptoms, is provided by plaques (known as Alzheimer's fibrils). These protein aggregates consist largely of incorrectly folded amyloid beta peptide (also known as Abeta peptide or amyloid beta peptide) and are deposited in the brain of Alzheimer's patients (as described by Walsh and Selkoe: Journal of Neurochemistry 101: pp 1172-1184 (2007)) and are the result of an increased clustering of the amyloid beta peptide in the brain. The amyloid beta peptide fibrils are, however, only the final stage of a process which begins with the cleavage of monomeric amyloid beta peptide from APP (amyloid precursor protein), continues with the formation of neurotoxic amyloid beta peptide oligomers, and only then ends with amyloid beta peptide fibrils.

In order to prevent the clustering with the amyloid beta peptide, there are experimental therapies of active and passive immunization with the amyloid beta peptide fragment as an immunogen.

Experimental therapies are carried out in in vitro models of amyloid beta peptide aggregation, in cell models of amyloid beta peptide production, and also in transgenic mouse models which form amyloid beta peptide aggregates in the brain. More particularly, active and passive immunization as a therapy were carried out in the transgenic mouse model of amyloid beta peptide aggregation (as described by Schenk et al.: Nature (1999) and by Bard et al. (2003)). In the first description of active immunization, full-length L-amyloid beta peptide was used as an immunogen and resulted in clearance of the plaques in a mouse model of Alzheimer's disease in the context of an immunization (as described by Schenk et al., Nature (1999)). In a similar mouse model, passive immunization was also successfully applied. It became apparent that N-terminal epitopes in the region of amyloid beta peptide 1-11 were especially efficient in giving rise to cerebral clearance of the amyloid beta peptide fibrils (as described by Bard et al.: PNAS 100(4), pp 2023-2028 (2003)). Currently, two studies of passive immunization, for example, antibodies/antibody fragments, in patients with Alzheimer's disease are taking place (as described by Brody and Holtzman: Annual Reviews in Neuroscience 31, pp 175-193 (2008)).

Immunization was tested with success in animal experiments, but active immunization in humans resulted in a T cell-mediated autoimmune response or autoimmune disease, in which the endogenous immune system caused meningoencephalitis in the brain of the patient (as described by Brody and Holtzman: Annual Reviews in Neuroscience 31, pp 175-193 (2008)). Active immunization with the amyloid beta peptide fragment is therefore currently considered not to be promising.

Antibodies to the amyloid beta peptide for passive immunotherapy have been described by Bard et al. (PNAS 100(4), pp 2023-2028), by Dodel et al. (Ann Neurol 52, pp 253-256 (2002)), and in 2007 by Gardberg et al. (PNAS 104(40), pp 15659-15664 (2007)) to amino acids 1-8 of the amyloid beta peptide.

The immunization of old beagles with complete (1-42) fibrillar amyloid beta peptide has, for example, also been described by Head et al. (The Journal of Neuroscience 28(14), pp 3555-3566 (2008)). Differences between dogs and humans with respect to the use of the amyloid beta peptide as an immunogen exist, however, since, compared with humans, dogs show no counteractive autoimmune response.

Cribbs et al. (The Journal of Biological Chemistry 272(11), pp 7431-7436 (1997)) described the mechanism of the amyloid beta peptide and used the D- and L-isomers of the complete amyloid beta peptide and also a truncated form (amino acids 1-42 or 25-35). The stereospecificity was likewise described by Esler et al. The detection of proteins having an altered conformation/prions by using sequences which correspond to the target protein to be detected was described in US 2008/0171341 A1.

WO 02/081505 A2 describes the implementation of a phage display for identifying amino acid sequences which bind to the Ass peptide. U.S. Pat. No. 6,689,752 B2 describes the influence of sequences consisting of 3-5 amino acids on the aggregation of amyloid beta peptide.

Cribbs et al. described that neurotoxicity is not stereoisomer-specific. No tests for an immune response were, however, made, but reference was made to the lower immunogenicity of the D-isomers.

Geylis et al. described cell lines obtained from healthy human subjects which synthesize antibodies which bind to amino acids 1-16 of the amyloid beta peptide and the use thereof in passive immunization. Lee et al. (American Neurological Association 58, pp 430-435 (2005)) described the antibody sera from human subjects who did or did not develop meningoencephalitis after amyloid beta peptide immunization. A result of this investigation was that the antibodies were mainly directed against amino acids 1-8 of the amyloid beta peptide.

SUMMARY

An aspect of the present invention is to provide a composition for use as a therapeutic in the preventive treatment or therapy of protein aggregation/misfolding diseases. Another alternative aspect of the present invention is to provide a use of the composition in a process for active immunization against Alzheimer's disease and other protein aggregation diseases so as to selectively evoke a B cell immune response while avoiding a T cell immune response.

In an embodiment, the present invention provides a composition which includes D-peptides or antibodies to at least one of prevent a disease and treat the disease, wherein the D-peptides interact with an amyloid peptide and the antibodies bind to both the D-peptide and the amyloid peptide.

BRIEF DESCRIPTION OF THE DRAWINGS

The present invention is described in greater detail below on the basis of embodiments and of the drawings in which.

DETAILED DESCRIPTION

Figure 1:
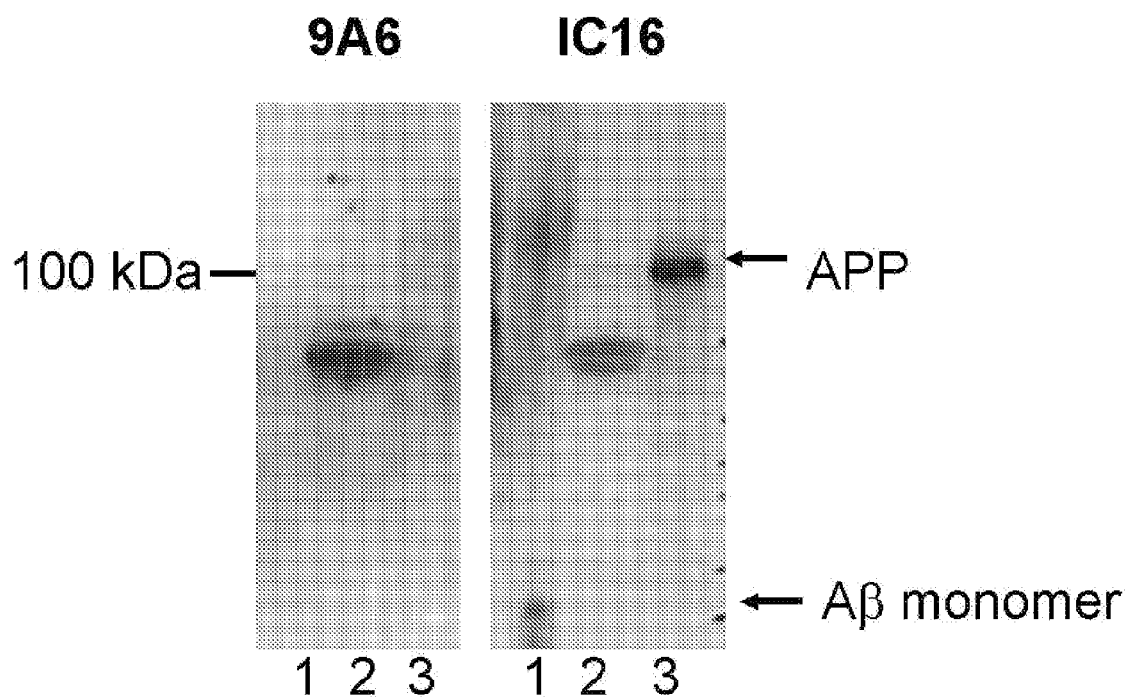
FIG. 1 shows a Western blot of synthetic amyloid beta peptide (1) and CHO cells, transfected with APP (3); irrelevant control (2). This Western blot shows that 9A6 does not recognize APP or amyloid beta peptide on the Western blot (left-hand side), whereas the universal anti-amyloid beta peptide antibody IC16 is able to do this (right-hand side).

In an embodiment of the present invention, the composition comprises a D-peptide as an immunogen which interacts with an amyloid beta peptide and elicits the antibody formation of anti-amyloid beta peptide antibodies. The composition can also comprise an amyloid beta peptide-interacting antibody, wherein this antibody is capable of binding to the abovementioned D-peptide and additionally to the amyloid beta peptide. The "interaction" between the D-peptide and the amyloid beta peptide is a protein-protein interaction.

The "composition" according to the present invention can, for example, be a vaccine, a drug (for example, in tablet form), an injectable solution, a foodstuff or a food supplement. The composition according to the present invention can consist only of D-peptides or only of antibodies, accompanied by the auxiliary agents required for the particular administration, such as, for example, salts such as aluminum salts, buffers, or solvents.

Further advantages over the prior art are, for example:
a low molecular weight of the immunogen;
no T cell response (cellular autoimmunity) and thus distinctly fewer secondary effects;
the use of low amounts of the composition since a delay in degradation of the immunogen exists; and
the immunogen is simple to modify or to combine.

By means of the composition according to the present invention, immunization with D-peptides leads to the generation of amyloid beta peptide-specific antibodies. This immunization with a D-peptide immunogen different from an amyloid beta peptide is superior to the amyloid beta peptide immunogen, since an antibody response against the amyloid beta peptide is evoked without the anti-amyloid beta peptide T cell immune response occurring at the same time and causing secondary effects.

"Immunization" means, for example, the generation of an immune response against a defined antigen with the goal of eliminating this antigen, of neutralizing it, and/or of otherwise rendering it harmless to the organism. Active immunization: introduction of an antigen (usually a peptide sequence) such that an endogenous immune response is generated which results in the elimination of the antigen and, above all, related antigens.

"Passive immunization" means, for example, the parenteral introduction of antibodies, which results in elimination of the antigen.

The composition according to the present invention can prevent the formation of amyloid beta peptide multimers owing to binding of an antibody to the multimerization domain of the amyloid beta peptide, wherein the antibody is formed after immunization with a D-peptide.

"Amyloid beta peptide multimers" mean for the purpose of the present invention, for example, the stable assembly of multiple amyloid beta peptide molecules with the attainment of new functions ("gain of function").

The term "multimerization domain" defines, for example, those domains of the amyloid beta peptide which relate to the interaction of the amyloid beta peptides with one another. In an embodiment, amino acids 10-42 of the amyloid beta peptide fulfill this function.

A further indication area is the use in the therapy of Alzheimer's disease, diabetes mellitus, and other amyloid diseases, and also diseases in which the homomultimerization of a protein is important, such as, for example, Parkinson's disease, frontotemporal dementia, amyotrophic lateral sclerosis, cystic fibrosis, and certain forms of epilepsy.

In an embodiment, the present invention further provides a composition in which the D-peptide:
a) contains a retro-inverse sequence of the amyloid beta peptide or amyloid beta peptide subfragments and consists entirely of D-amino acids; and/or
b) binds to the multimerization domain of the amyloid beta peptide; and/or
c) contains the sequence SEQ ID NO:1 or SEQ ID NO:2 and consists entirely of D-amino acids; and/or
d) contains D-peptides having the sequence SEQ ID NO:1 or SEQ ID NO:2, wherein the D-peptides having the sequence SEQ ID NO:1 or SEQ ID NO:2 partly comprise L-amino acids; and/or
e) contains sequences homologous to SEQ ID NO:1 or SEQ ID NO:2.

"D-peptides" consist, in one variant, of a retro-inverse sequence for amyloid beta peptide, or amyloid beta peptide subfragments and entirely of D-amino acids.

A "subfragment" consists of 3, 4, 5, 6, 7, 8, 9, 10, 11, 12, 13, 14, 15, 16, or more amino acids homologous to the amino acid sequence of the amyloid beta peptide.

In an embodiment of the present invention, the D-peptides according to the present invention bind to the multimerization domain of the amyloid beta peptide. In an embodiment of the present invention, the D-peptides have the sequence SEQ ID NO:1 or SEQ ID NO:2 and consist entirely of D-amino acids. In an embodiment of the present invention, the D-peptides have the sequence SEQ ID NO:1 or SEQ ID NO:2, and partly comprise L-amino acids. In an embodiment of the present invention, the D-peptides have homologous sequences with respect to SEQ ID NO:1 or SEQ ID NO:2. "D-peptide" means, for example, a peptide which is composed of amino acids in the D-form.

"Partly" comprise L-amino acids means that 1, 2, 3, 4, 5, 6, 7, 8, 9, 10, or more amino acids homologous to the amino acid sequence of the D-peptide consisting of D-amino acids are replaced in each case with the same amino acid in the L-conformation.

"Homologous sequences" means, for the purpose of the present invention, that an amino acid sequence is at least 70%, 75%, 80%, for example, 85%, 90%, or, for example, 91%, 92%, 93%, 94%, 95%, 96%, 97%, 98%, or 99%, identical to SEQ ID NO:1 or SEQ ID NO:2. Sequences homologous to the sequences according to the present invention consisting of D-amino acids may also partly comprise L-amino acids. Instead of the term "identity," the present description uses the terms "homologous" or "homology" synonymously. The identity between two nucleic acid sequences or polypeptide sequences is calculated by means of a comparison with the aid of the program BESTFIT based on the algorithm of Smith, T. F. and Waterman, M. S. (as described in Adv. Appl. Math. 2, pp 482-489 (1981)) with the setting of the following parameters for amino acids: gap creation penalty of 8 and gap extension penalty of 2; and the following parameters for nucleic acids: gap creation penalty of 50 and gap extension penalty of 3. The identity between two nucleic acid sequences or polypeptide sequences can, for example, be defined by means of the identity of the nucleic acid sequence/polypeptide sequence across the entire sequence length in each case, as calculated by means of a comparison with the aid of the program GAP based on the algorithm of Needleman, S. B. and Wunsch, C. D. (as described in J. Mol. Biol. 48, pp 443-453) with the setting of the following parameters for amino acids: gap creation penalty of 8 and gap extension penalty of 2; and the following parameters for nucleic acids: gap creation penalty of 50 and gap extension penalty of 3.

These homologous D-peptides bind either to the amyloid beta peptide and/or the amyloid beta peptide multimerization domain. They may be derived (homologous) from the amyloid beta peptide and are functionally defined, i.e., are capable of evoking an immune response identical at least to the amyloid beta peptide. They are not, however, the amyloid beta peptide itself and generate an antibody response in mice against the amyloid beta peptide and/or amyloid beta peptide multimers.

The term "retro-inverse peptide" or "retro-inverso peptide" means, according to the present invention, for example, a peptide composed of amino acids in the D-form (inverse: chirality of the alpha-carbon atom inverse to the L-form) in which additionally the sequence order of the original peptide has been reversed (retro=reversed; as described in Regenmortel and Muller: Current Opinion in Biotechnology 9, pp 377-382 (1998)).

In an embodiment, the present invention provides a composition comprising antibodies, wherein the antibody binds to the amyloid peptide or amyloid beta peptide, and:
a) binds to a retro-inverse sequence of the amyloid beta peptide or amyloid beta peptide subfragments; and/or
b) binds to the multimerization domain of the amyloid beta peptide and also to the amyloid beta peptide; and/or
c) binds to SEQ ID NO:1 or SEQ ID NO:2 or homologous sequences thereof.

The antibodies can, for example, have the properties of the amyloid beta peptide itself and compete with the multimerization of the amyloid beta peptide if, for antibody generation, use is made of peptides which bind to the amyloid beta peptide multimerization domain.

In an embodiment, the present invention provides a process for preparing the composition according to the present invention, wherein antibody-producing hybrid cells are obtained by immunizing animals or animal cells and fusing animal cells with myeloma cells with subsequent selection and culturing, and antibodies are isolated and cleaned up.

The immunization, fusion, selection, culturing of antibody-producing hybrid cells and the antibody isolation or antibody cleanup can, for example, be carried out with the methods as described in "Monoclonal antibodies" (Heddy Zola: Springer Verlag, New York (2000)) and methods known to a person skilled in the art. Further processes, more particularly for the screening of antibody-producing cells, have been described by Korth et al., in Methods in Enzymology 309, pp 106 et seq. (1999).

For the immunization, use can, for example, be made of animals (or animal cells), such as mice, rabbits, rats, guinea pigs, and further animals used routinely for antibody production. If mice are chosen for immunization with the composition according to the present invention, an immunization strategy may be as follows: the composition can be injected subcutaneously (for example, three times; day 0: complete Freund's adjuvant; days 21 and 22: incomplete Freund's adjuvant; withdrawal of about 100 µl of blood on day 31). After one or more booster injections with the composition according to the present invention, the mice can, for example, be anesthetized on day 50, decapitated, and the spleen removed. The spleen cells obtained in this way (splenocytes) can be mixed with mouse myeloma cells in a ratio of 1:5 and fused by adding 50% polyethylene glycol (PEG) (8 minutes, room temperature). The cells can then be washed and cultured overnight. The selection for antibody-producing hybridoma cells can, for example, be carried out in HAT medium and in 96-well microtiter plates and in an ELISA enzyme test.

In an embodiment, the present invention provides the use of a composition according to the present invention for preventing amyloid beta peptide multimers. Use can be made here of D-peptides or antibodies which bind to the multimerization domain of the amyloid beta peptide.

In an embodiment of the present invention, the composition comprises 10-1000 µg of immunogen. In an alternative embodiment, the composition comprises 20-900, 25-750, 30-600, 40-500, 50-400, 50-300, or 50-250 µg of immunogen. It would also be conceivable for a composition to comprise less than 10 µg of immunogen or more than 1000 µg of immunogen.

"Immunogen" means, for example, an antigen resulting in immunity. An immunogen is a substance which is capable of triggering an immune response. Immunogens thus differ from the antigens which are recognized by an antibody, but of which not all are able to trigger an immune response on their own.

"Immunity" means, for example, the altered readiness for reaction of the immune system toward antigens (such as, for example, viruses, bacteria, or foreign protein) which is caused by immunization and is characterized by the appearance of specific antibodies and/or cells.

In an embodiment, the present invention further provides the use of the composition according to the present invention in the prevention and/or therapy of Alzheimer's disease. D-peptides which bind to the multimerization domain of the amyloid beta peptide can thus be used to produce a drug for the prevention and/or therapy of Alzheimer's disease.

In an embodiment, the present invention provides a use of the composition according to the present invention comprising D-peptides as a therapeutic and/or for the disease prevention of Alzheimer's disease, wherein the D-peptide:
a) contains a retro-inverse sequence of the amyloid beta peptide or amyloid beta peptide subfragments and consists entirely of D-amino acids; and/or
b) binds to the multimerization domain of the amyloid beta peptide; and/or
c) contains the sequence SEQ ID NO:1 or SEQ ID NO:2 and consists entirely of D-amino acids; and/or d) contains the sequence SEQ ID NO:1 or SEQ ID NO:2, wherein the D-peptides having the sequence SEQ ID NO:1 or SEQ ID NO:2 partly comprise L-amino acids; and/or
e) contains sequences homologous to SEQ ID NO:1 or SEQ ID NO:2.

In an embodiment, the present invention provides the use of a composition according to the present invention comprising antibodies as a therapeutic and/or for the disease prevention or for the diagnosis of Alzheimer's disease, wherein the antibodies:
a) bind to a retro-inverse sequence of the amyloid beta peptide or amyloid beta peptide subfragments; and/or
b) bind to the multimerization domain of the amyloid beta peptide and also to the amyloid beta peptide; and/or
c) bind to SEQ ID NO:1 or SEQ ID NO:2 or homologous sequences thereof.

In an embodiment, the present invention provides a use of a composition comprising antibodies for the diagnosis of Alzheimer's disease, for the detection or quantification of biomolecules, or for the localization of biomolecules in tissues, cells, or contains in the recognition of specific cell types, wherein the antibody:
a) binds to a retro-inverse sequence of the amyloid beta peptide or amyloid beta peptide subfragments and also to the amyloid beta peptide; and/or
b) binds to the multimerization domain of the amyloid beta peptide; and/or
c) binds to SEQ ID NO:1 or SEQ ID NO:2 or homologous sequences thereof and also to the amyloid beta peptide.

Detection or quantification of biomolecules, for the purpose of the present invention, means the determination of substances by means of antigen-antibody reactions (for example, immunoassays).

The localization of biomolecules in tissues or cells or the recognition of specific cell types, for the purpose of the present invention, means the use of antibodies in, for example, immunohistochemistry or immunocytochemistry.

An advantage of the present invention is that a therapeutic antibody response is evoked without the D-peptide used in this case being processed by T cells.

The method of the present invention therefore makes it possible to easily develop immunization strategies against protein aggregation diseases or protein conformation diseases. A process related to the therapy of Alzheimer's disease, in which amyloid beta peptide-interacting D-peptides are employed in immunization, can thus achieve, in an individual, a humoral immune response which neutralizes amyloid beta peptide toxicity and/or clears amyloid beta peptide. Processes can furthermore be developed which concern a disease other than Alzheimer's disease, in which the aggregation or multimerization of proteins is likewise—relevant to the disease and in which D-peptides binding to multimerization interfaces are used (protein conformation diseases of the CNS, diabetes, etc.).

"Clearing" or "clearance" means, for example, the removal of a particular exogenous or endogenous substance from a tissue performed specifically by an organ (for example, renal clearance), a cellular component (for example, macrophages, microglia), or subcellular compartments (for example, proteasome).

A further advantage of the present invention is that, additionally, the epitope space of the amyloid beta peptide is forsaken, which can in principle limit the humoral immune response at high self-tolerance. In the use according to the present invention of amyloid beta peptide-binding D-peptides, the T cell immune response is also suppressed, since these peptides cannot be degraded and displayed.

The present invention also provides antibodies which are directed to the amyloid beta peptide multimerization domain and prevent multimerization of the amyloid beta peptide. Owing to labeling with the antibody, amyloid beta peptides or the assembled amyloid beta peptide deposits can subsequently be degraded by the endogenous immune system. Further antibodies according to the present invention are directed to the amyloid beta peptide in general and not specifically to the multimerization domain.

EXAMPLES

Example 1 (Immunization of Mice with D3 Peptide)

Mice were immunized with D-peptides. Use was made of the D3 peptide and also a retro-inverse peptide of the amyloid beta peptide (riAbeta1-16; retro-inverso-Abeta(1-16)). After multiple booster injections (booster effect), fusion to generate monoclonal antibodies was carried out according to standard methods. It was possible to isolate monoclonal antibodies which bind to D3, riAbetal-16, and to the amyloid beta peptide. The immunization with the mentioned D-peptides thus leads to a protective immune response against the amyloid beta peptide.

"Booster effect" (achieved by a booster injection) means, for example, an immunological secondary reaction or an enhanced immune response after repeated contact with the antigen.

The peptides used for immunization had the following sequences:

```
                                           (SEQ ID NO: 1)
"D3" peptide:              rprtr lhthr nr (SEQ ID NO: 2)
retro-inverso-Abeta(1-16): kqhhv eygsd hrfea d
```

D3 was covalently bonded (crosslinking) to KLH (keyhole limpet hemocyanin) and immunized mice with standard procedures. These were then fused with mouse myeloma cells according to standard protocols. The cell culture supernatant of the resulting hybridoma cells were then tested for the recognition of both the D3 peptide and the amyloid beta peptide in a standard ELISA.

The following clones recognize D3 only (and not the amyloid beta peptide):

4G11, 13H11, 32A11, 40B7

The following clones recognize both D3 and the amyloid beta peptide:

9A6, 14B5, 39B12

These experiments demonstrate that:
1. The immunization with D3 results in an antibody response against the amyloid beta peptide; and
2. That there is a binding site on certain antibodies which is able to recognize both the amyloid beta peptide and D3.

Figure 2:
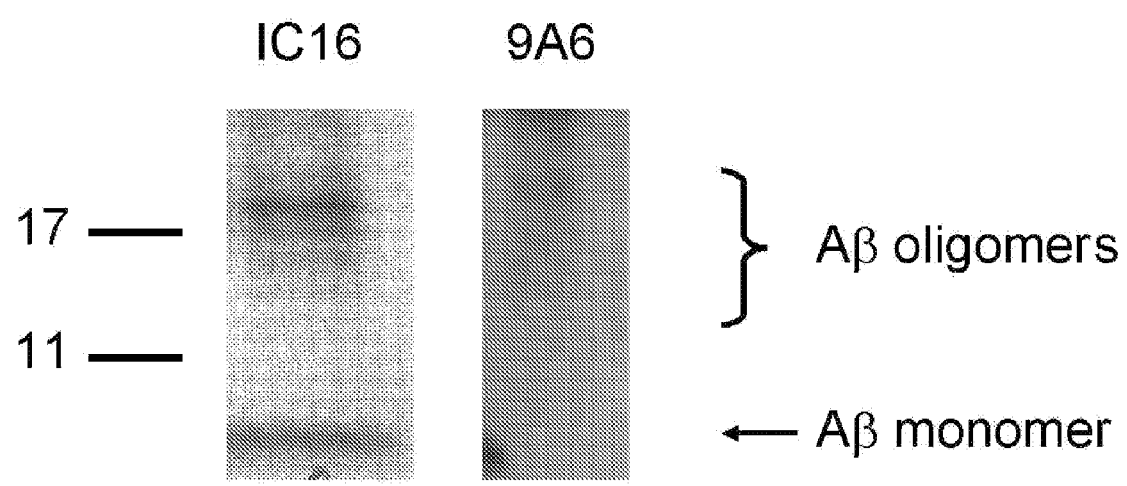
FIG. 2 shows a Western blot of an immunprecipitation by IC16 (left-hand side) and 9A6 (right-hand side) from the supernatant of CHO cells permanently transfected with APP, which secrete the amyloid beta peptide. It can be seen that 9A6 recognizes amyloid beta peptide oligomers.
Figure 3:
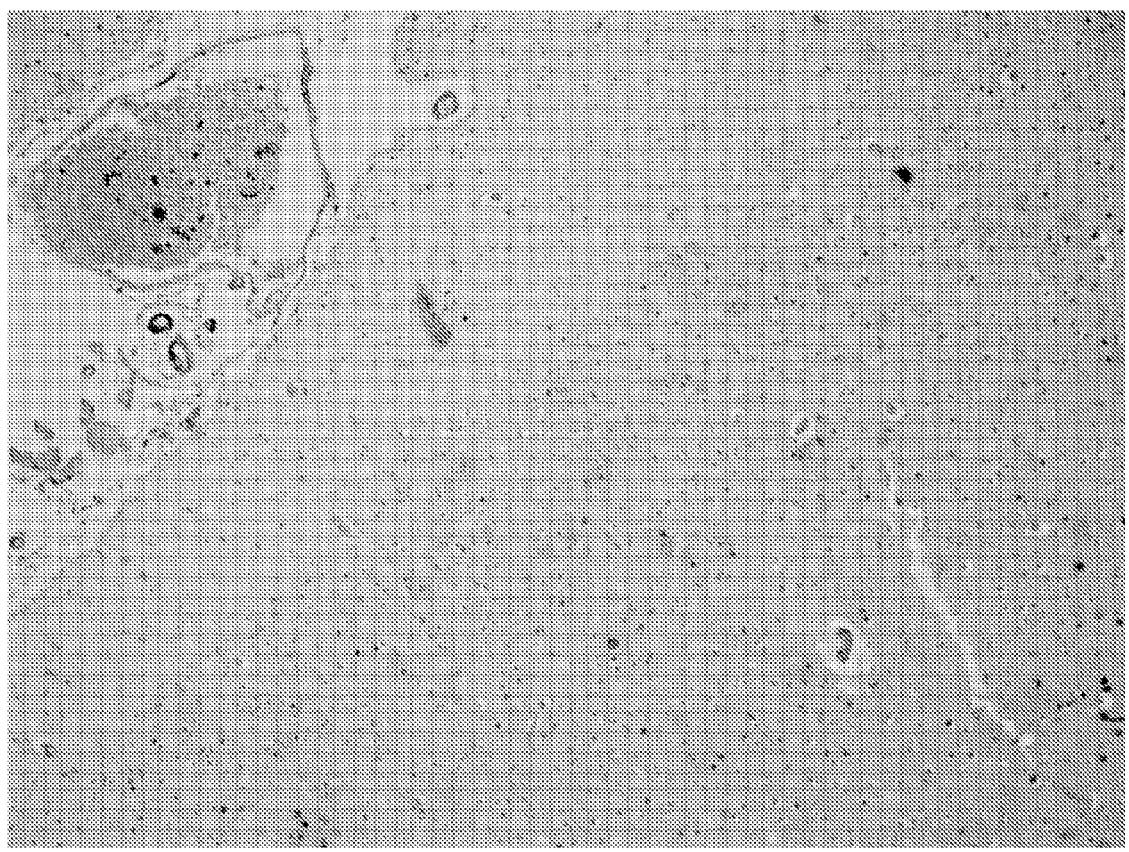
FIG. 3 shows an immunohistochemical stain with 9A6 of a cortical sample from a patient with Alzheimer's disease. It can be seen that the 9A6 antibody weakly recognizes amyloid beta peptide plaques.

The anti-D3/anti-amyloid beta peptide antibody 9A6, which was investigated by way of example, was further tested in the assays shown in FIG. 1, FIG. 2, and FIG. 3.

The present invention is not limited to embodiments described herein; reference should be had to the appended claims.

The invention claimed is:

1. A composition comprising a peptide, wherein the peptide is a D-peptide, interacts with an amyloid peptide, is suitable for therapy of Alzheimer's disease and is at least one of
   (a) the peptide of SEQ ID NO:2 which consists of D-amino acids;
   (b) peptide (a), wherein a part of the D-amino acids is replaced by L-amino acids;
   (c) peptide (a), wherein up to 10% of the sequence are different from SEQ ID NO:2.

2. The composition of claim 1, wherein the composition comprises at least peptide (a).

3. The composition of claim 1, wherein the composition comprises at least peptide (b).

4. The composition of claim 1, wherein the composition comprises at least peptide (c).

5. The composition of claim 1, wherein the composition does not elicit a T-cell autoimmune response.

6. The composition of claim 2, wherein the composition does not elicit a T-cell autoimmune response.

7. The composition of claim 3, wherein the composition does not elicit a T-cell autoimmune response.

8. The composition of claim 4, wherein the composition does not elicit a T-cell autoimmune response.

* * * * *